US012797139B2

(12) United States Patent
Hiasa

(10) Patent No.: US 12,797,139 B2
(45) Date of Patent: Nov. 17, 2026

(54) SUPPORT DEVICE, SUPPORT METHOD, AND SUPPORT PROGRAM

(71) Applicant: FUJIFILM CORPORATION, Tokyo (JP)

(72) Inventor: Yuta Hiasa, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 19/057,991

(22) Filed: Feb. 20, 2025

(65) Prior Publication Data

US 2025/0295455 A1 Sep. 25, 2025

(30) Foreign Application Priority Data

Mar. 21, 2024 (JP) ................................ 2024-045745

(51) Int. Cl.
*A61B 34/20* (2016.01)
*A61B 6/00* (2024.01)
*A61B 6/46* (2024.01)

(52) U.S. Cl.
CPC .............. *A61B 34/20* (2016.02); *A61B 6/466* (2013.01); *A61B 6/487* (2013.01)

(58) Field of Classification Search
CPC ......... A61B 34/20; A61B 6/466; A61B 6/487; A61B 2017/00809; A61B 2090/364; A61B 34/10; A61B 2034/107; A61B 2090/376; A61B 2090/3762; A61B 2090/3764
See application file for complete search history.

(56) References Cited

U.S. PATENT DOCUMENTS

2007/0092864 A1* 4/2007 Reinhardt ................ G06T 7/11 600/300
2020/0015905 A1 1/2020 Scheib et al.
2020/0078103 A1 3/2020 Duindam et al.
2023/0165638 A1* 6/2023 Mansi .................... A61B 34/10 604/500

(Continued)

FOREIGN PATENT DOCUMENTS

CN 113194813 A 7/2021
CN 114027987 A 2/2022

(Continued)

OTHER PUBLICATIONS

Extended European Search Report dated Sep. 11, 2025, issued in corresponding EP Patent Application No. 25164864.8.

*Primary Examiner* — Alexei Bykhovski
(74) *Attorney, Agent, or Firm* — SOLARIS Intellectual Property Group, PLLC

(57) ABSTRACT

A support device is a device that supports insertion of a medical instrument into a tubular structure, and the support device acquires a two-dimensional medical image, and a three-dimensional pathway that is three-dimensional information on a pathway through which the medical instrument passes, derives a first feature amount representing a relationship between a reference point in a three-dimensional space and the three-dimensional pathway, performs control of displaying a composite image in which the three-dimensional pathway is superimposed on the two-dimensional medical image, and varies a display aspect of the three-dimensional pathway in the composite image according to the first feature amount.

18 Claims, 6 Drawing Sheets

(56) References Cited

U.S. PATENT DOCUMENTS

| | | | | |
|---|---|---|---|---|
| 2023/0200790 | A1* | 6/2023 | Duindam | A61B 1/00097 600/424 |
| 2024/0206981 | A1* | 6/2024 | Knutson | A61B 34/10 |
| 2024/0407755 | A1 | 12/2024 | Masumoto | |

FOREIGN PATENT DOCUMENTS

| | | | | |
|---|---|---|---|---|
| EP | 3815613 | A1 * | 5/2021 | A61B 90/37 |
| WO | 2022/251715 | A2 | 12/2022 | |
| WO | 2023/162657 | A1 | 8/2023 | |

* cited by examiner

SUPPORT DEVICE, SUPPORT METHOD, AND SUPPORT PROGRAM

CROSS-REFERENCE TO RELATED APPLICATIONS

This application claims priority from Japanese Patent Application No. 2024-045745, filed on Mar. 21, 2024, the entire disclosure of which is incorporated herein by reference.

BACKGROUND

1. Technical Field

The present disclosure relates to a support device, a support method, and a support program.

2. Description of the Related Art

WO2023/162657A1 discloses a technology of displaying a composite image in which preoperative preparation information is superimposed on a two-dimensional surgical field image captured by an endoscope, on a display.

SUMMARY

In the medical field, a medical instrument is inserted into a tubular structure. For example, there is a procedure called a transbronchial lung biopsy, in which a definitive diagnosis of lung cancer is performed by combining preoperative computed tomography (CT) images, a bronchoscope, and intraoperative X-ray images. In this procedure, in peripheral areas where the bronchoscope cannot be inserted, a practitioner performs a biopsy by inserting a treatment tool while referring to two-dimensional images obtained through X-ray fluoroscopy. In such a procedure, the difficulty of the procedure is relatively high due to the fact that it is not easy to ascertain the position of a lesion in a depth direction in the two-dimensional image, the visibility of the lesion having a relatively low cell density is low, and the like. Therefore, it is required to effectively support the procedure of inserting the medical instrument into the tubular structure.

The present disclosure has been made in view of the above circumstances, and an object of the present disclosure is to provide a support device, a support method, and a support program capable of effectively supporting a procedure of inserting a medical instrument into a tubular structure.

A support device according to a first aspect is a support device that includes at least one processor and supports insertion of a medical instrument into a tubular structure, in which the processor acquires a two-dimensional medical image, and a three-dimensional pathway that is three-dimensional information on a pathway through which the medical instrument passes, derives a first feature amount representing a relationship between a reference point in a three-dimensional space and the three-dimensional pathway, performs control of displaying a composite image in which the three-dimensional pathway is superimposed on the two-dimensional medical image, and varies a display aspect of the three-dimensional pathway in the composite image according to the first feature amount.

In the support device according to a second aspect, in the support device according to the first aspect, the processor acquires a three-dimensional position of a region of interest, derives a second feature amount representing a relationship between the reference point and the three-dimensional position of the region of interest, performs control of displaying the composite image in which the region of interest is superimposed on the two-dimensional medical image, and varies a display aspect of the region of interest in the composite image according to the second feature amount.

In the support device according to a third aspect, in the support device according to the first or second aspect, the processor acquires a visual line direction for projecting the three-dimensional pathway onto a two-dimensional plane, and the first feature amount is a feature amount representing a relative positional relationship between the reference point and the three-dimensional pathway in the visual line direction.

In the support device according to a fourth aspect, in the support device according to the second aspect, the processor acquires a visual line direction for projecting the three-dimensional pathway onto a two-dimensional plane, and the second feature amount is a feature amount representing a relative positional relationship between the reference point and the three-dimensional position of the region of interest in the visual line direction.

In the support device according to a fifth aspect, in the support device according to any one of the first to fourth aspects, the reference point is a point on the three-dimensional pathway.

In the support device according to a sixth aspect, in the support device according to the fifth aspect, the reference point is a position of the medical instrument on the three-dimensional pathway.

In the support device according to a seventh aspect, in the support device according to the sixth aspect, the medical instrument is an endoscope including a treatment tool, and the reference point is a position of the treatment tool on the three-dimensional pathway.

In the support device according to an eighth aspect, in the support device according to the sixth aspect, the medical instrument is an endoscope including a camera, and the reference point is a position of the camera on the three-dimensional pathway.

In the support device according to a ninth aspect, in the support device according to the first aspect, the first feature amount is a distance between the reference point and the three-dimensional pathway in the three-dimensional space.

In the support device according to a tenth aspect, in the support device according to the second aspect, the reference point is the three-dimensional position of the region of interest.

In the support device according to an eleventh aspect, in the support device according to any one of the first to tenth aspects, the processor acquires a focused pathway on the three-dimensional pathway, and in the control of displaying the composite image, performs control of displaying the focused pathway in an emphasized manner as compared with a pathway other than the focused pathway on the three-dimensional pathway.

In the support device according to a twelfth aspect, in the support device according to the eleventh aspect, the focused pathway is a pathway connecting the reference point to a point at which a distance to the region of interest on the three-dimensional pathway is equal to or less than a threshold value.

In the support device according to a thirteenth aspect, in the support device according to the eleventh aspect, the focused pathway is a pathway registered in advance as preoperative information.

In the support device according to a fourteenth aspect, in the support device according to any one of the first to thirteenth aspects, a pathway through which the medical instrument passes is a bronchial lumen.

In the support device according to a fifteenth aspect, in the support device according to any one of the first to fourteenth aspects, the two-dimensional medical image is an image obtained by radiographic fluoroscopy.

In the support device according to a sixteenth aspect, in the support device according to any one of the first to fourteenth aspects, the three-dimensional pathway is a bronchial lumen in a three-dimensional medical image, and the two-dimensional medical image is a virtual radiation image generated from the three-dimensional medical image.

In the support device according to a seventeenth aspect, in the support device according to any one of the first to sixteenth aspects, the processor acquires a three-dimensional medical image including a pathway through which the medical instrument passes, deforms the three-dimensional medical image by performing registration of the three-dimensional medical image and the two-dimensional medical image, and acquires the three-dimensional pathway on the basis of the deformed three-dimensional medical image.

A support method according to an eighteenth aspect is a support method of processing executed by a processor of a support device that includes at least one processor and supports insertion of a medical instrument into a tubular structure, the processing including acquiring a two-dimensional medical image, and a three-dimensional pathway that is three-dimensional information on a pathway through which the medical instrument passes; deriving a first feature amount representing a relationship between a reference point in a three-dimensional space and the three-dimensional pathway; performing control of displaying a composite image in which the three-dimensional pathway is superimposed on the two-dimensional medical image; and varying a display aspect of the three-dimensional pathway in the composite image according to the first feature amount.

A support program according to a nineteenth aspect is a support program for causing a processor of a support device that includes at least one processor and supports insertion of a medical instrument into a tubular structure, to execute processing including acquiring a two-dimensional medical image, and a three-dimensional pathway that is three-dimensional information on a pathway through which the medical instrument passes; deriving a first feature amount representing a relationship between a reference point in a three-dimensional space and the three-dimensional pathway; performing control of displaying a composite image in which the three-dimensional pathway is superimposed on the two-dimensional medical image; and varying a display aspect of the three-dimensional pathway in the composite image according to the first feature amount.

According to the present disclosure, it is possible to effectively support a procedure of inserting a medical instrument into a tubular structure.

DETAILED DESCRIPTION

Hereinafter, embodiments for implementing the disclosed technology will be described in detail with reference to the drawings.

Figure 1:
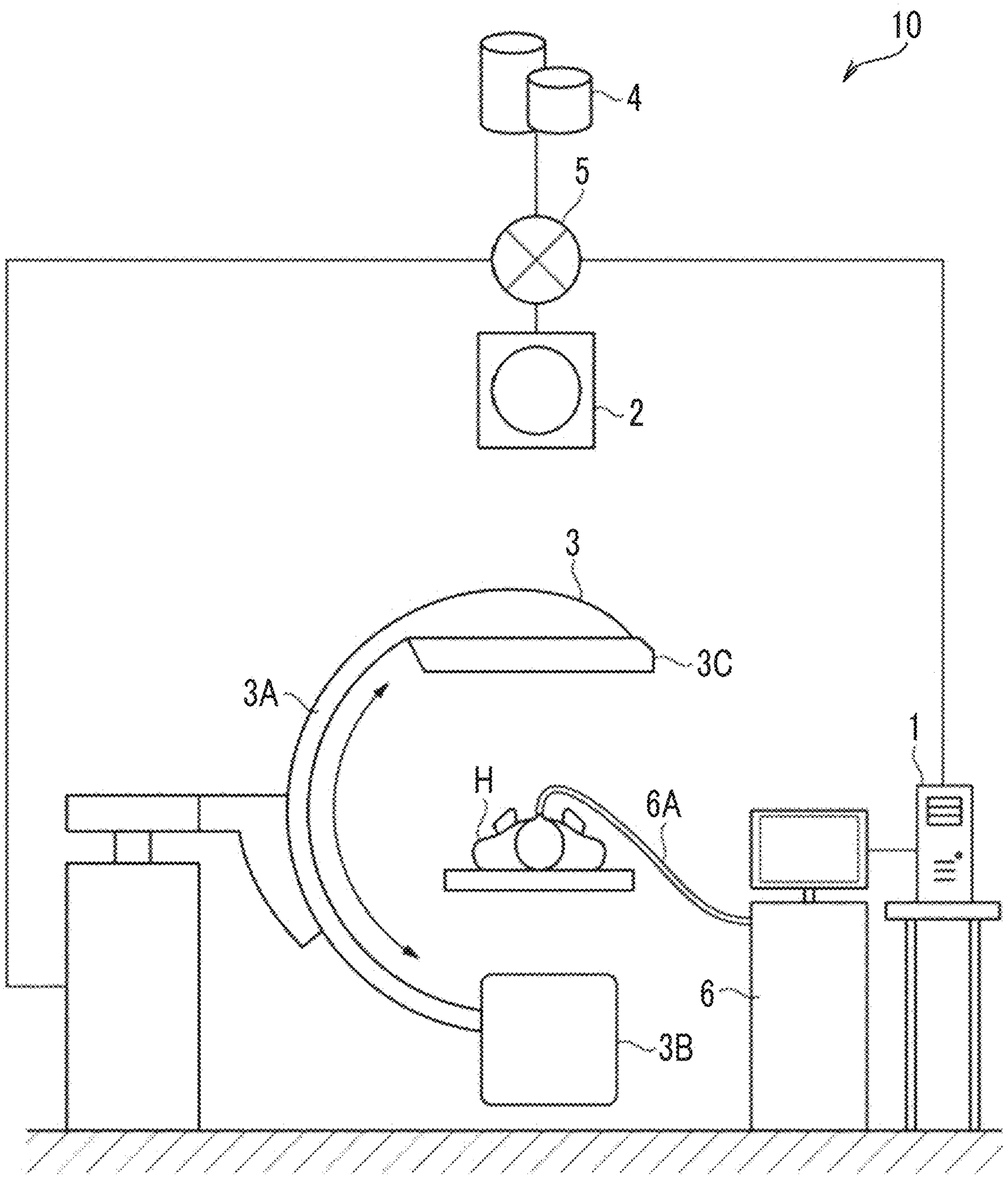
FIG. 1 is a diagram illustrating an example of a medical information system.

First, a configuration of a medical information system 10 will be described with reference to FIG. 1. As illustrated in FIG. 1, a medical information system 10 includes a support device 1, a three-dimensional image capturing device 2, a fluoroscopic image capturing device 3, and an image storage server 4. The support device 1, the three-dimensional image capturing device 2, the fluoroscopic image capturing device 3, and the image storage server 4 are connected to each other in a communicable state via a network 5.

The three-dimensional image capturing device 2 generates a three-dimensional medical image representing a site that is a diagnosis target of a subject H, by imaging the site. Examples of the three-dimensional image capturing device 2 include a CT device, a magnetic resonance imaging (MRI) device, and a positron emission tomography (PET) device. The three-dimensional medical image which is generated by the three-dimensional image capturing device 2 and consists of a plurality of tomographic images is transmitted to and stored in the image storage server 4. Note that in the present embodiment, a case where a target site of the subject H is a lung and the three-dimensional image capturing device 2 is a CT device will be described as an example. That is, the three-dimensional medical image according to the present embodiment is a CT image. In addition, in the present embodiment, it is assumed that a three-dimensional medical image including the chest of the subject His acquired in advance by imaging the chest of the subject H with the three-dimensional image capturing device 2 before a treatment for the subject H.

The fluoroscopic image capturing device 3 includes a C-arm 3A, an X-ray source 3B, and an X-ray detector 3C. The X-ray source 3B and the X-ray detector 3C are respectively attached to both end parts of the C-arm 3A. In the fluoroscopic image capturing device 3, the C-arm 3A is configured to be rotatable and movable such that the subject H can be imaged from any direction. Then, the fluoroscopic image capturing device 3 performs fluoroscopy in which the subject H is continuously irradiated with X-rays as an example of radiation according to a predetermined frame rate and the X-rays transmitted through the subject H are sequentially detected by the X-ray detector 3C, to sequentially acquire radiation images of the subject H, during the treatment for the subject H. In the following description, the radiation image of each of sequentially acquired frames will be referred to as a fluoroscopic image. The fluoroscopic image obtained by the radiographic fluoroscopy of the fluoroscopic image capturing device 3 is an example of a two-dimensional medical image according to the disclosed technology.

The image storage server 4 is a computer that stores and manages various kinds of data, and includes a large-capacity external storage device and software for database management. The image storage server 4 performs communication with another device via the network 5 in a wired or wireless manner, and transmits and receives image data and the like. Specifically, various kinds of data including image data indicating the three-dimensional medical image acquired by the three-dimensional image capturing device 2 and the fluoroscopic image acquired by the fluoroscopic image capturing device 3 is acquired via the network 5, and stored and managed in a recording medium such as a large-capacity external storage device. Note that a storage format of the image data and the communication between the devices via the network 5 are based on a protocol such as Digital Imaging and Communication in Medicine (DICOM).

In the present embodiment, a case of performing a biopsy treatment of cutting out a part of a lesion such as a lung nodule or the like present in the lung of the subject H while performing the fluoroscopy on the subject H and examining the presence of a disease in detail will be described as an example. Therefore, the fluoroscopic image capturing device 3 is disposed in a treatment room for performing a biopsy. In addition, an ultrasonic endoscope device 6 is installed in the treatment room. The ultrasonic endoscope device 6 includes an endoscope 6A to which a treatment tool such as an ultrasound probe and forceps are attached to a distal end thereof. In the present embodiment, in order to perform a biopsy of the lesion, an operator such as a doctor inserts the endoscope 6A into the bronchus of the subject H. In the biopsy, the fluoroscopic image capturing device 3 captures a fluoroscopic image of the subject H and displays the captured fluoroscopic image in real time, and the operator checks a distal end position of the endoscope 6A in the subject H in the fluoroscopic image and moves the distal end of the endoscope 6A to a position of the target lesion. The endoscope 6A is an example of a medical instrument according to the disclosed technology. The bronchial lumen is an example of a pathway through which the endoscope 6A according to the disclosed technology passes.

Here, lesions of the lung such as lung nodules occur outside the bronchus rather than inside the bronchus. Therefore, the operator moves the distal end of the endoscope 6A to the target position, and then performs a treatment of collecting a part of the lesion using a treatment tool such as forceps while checking the lesion position in an ultrasound image obtained by imaging the outside of the bronchus with the ultrasound probe.

In the present embodiment, the three-dimensional medical image and the fluoroscopic image are obtained by imaging an imaging range including a site that is a diagnosis target of the same subject H. That is, the imaging ranges of the three-dimensional image capturing device 2 and the fluoroscopic image capturing device 3 at least partially overlap each other. Therefore, the three-dimensional medical image obtained by the three-dimensional image capturing device 2 also includes the bronchial lumen that is the pathway through which the endoscope 6A passes.

Figure 2:
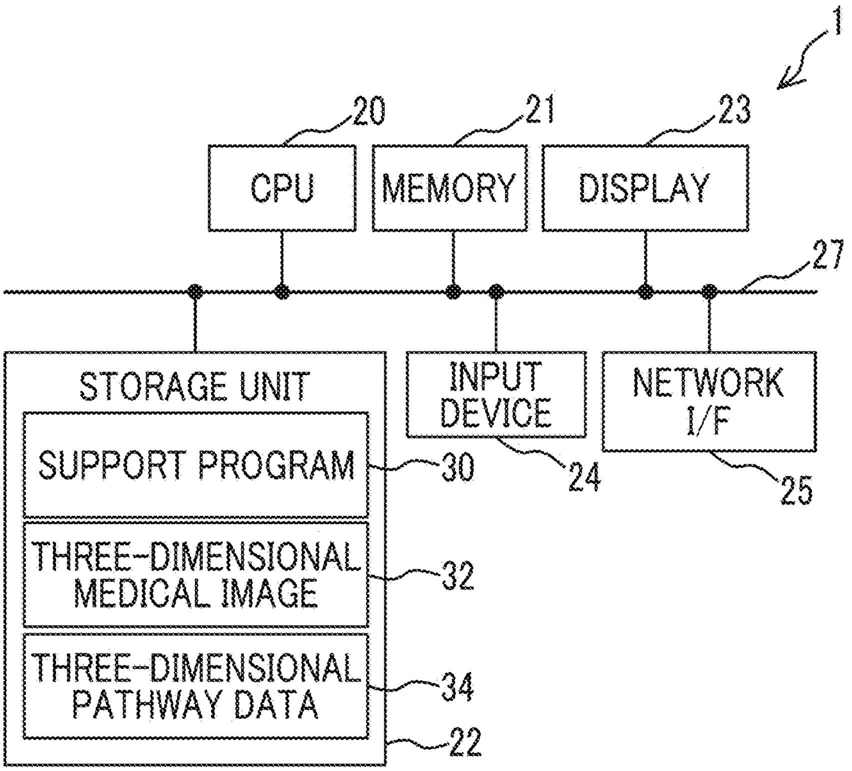
FIG. 2 is a block diagram illustrating an example of a hardware configuration of a support device.

Next, a hardware configuration of the support device 1 according to the present embodiment will be described with reference to FIG. 2. The support device 1 is a device that supports the insertion of the endoscope 6A into the bronchus as an example of the tubular structure. As illustrated in FIG. 2, the support device 1 includes a central processing unit (CPU) 20, a memory 21 as a temporary storage area, and a non-volatile storage unit 22. In addition, the support device 1 includes a display 23 such as a liquid crystal display, an input device 24 such as a keyboard and a mouse, and a network interface (I/F) 25 connected to the network 5. The input device 24 may be a touch panel integrated with the display 23. The CPU 20, the memory 21, the storage unit 22, the display 23, the input device 24, and the network I/F 25 are connected to a bus 27. The CPU 20 is an example of a processor according to the disclosed technology. Examples of the support device 1 include a computer such as a personal computer or a server computer.

The storage unit 22 is realized by a hard disk drive (HDD), a solid state drive (SSD), a flash memory, or the like. A support program 30 is stored in the storage unit 22 as a storage medium. The CPU 20 reads out the support program 30 from the storage unit 22, expands the support program 30 in the memory 21, and executes the expanded support program 30.

In addition, the storage unit 22 stores a three-dimensional medical image 32 and three-dimensional pathway data 34. The three-dimensional medical image 32 includes a tomographic image group obtained by imaging the subject H as a target of the biopsy. The three-dimensional medical image 32 is acquired from the image storage server 4 via the network 5 before the biopsy. Details of the three-dimensional pathway data 34 will be described below.

Figure 3:
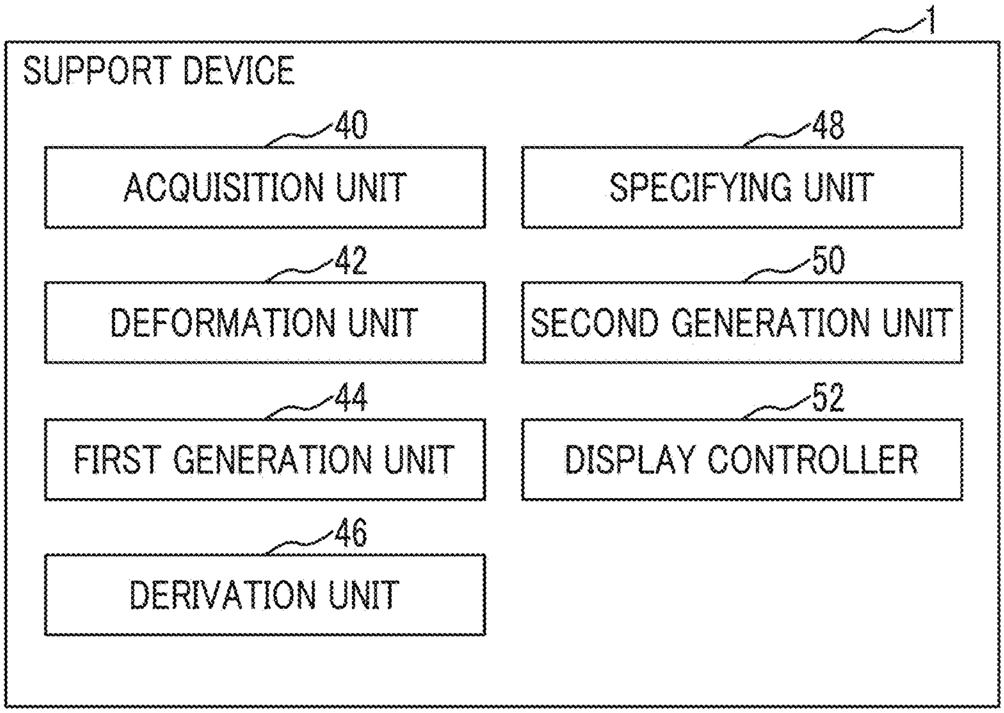
FIG. 3 is a block diagram illustrating an example of a functional configuration of the support device.

Next, a functional configuration of the support device 1 will be described with reference to FIG. 3. As illustrated in FIG. 3, the support device 1 includes an acquisition unit 40, a deformation unit 42, a first generation unit 44, a derivation unit 46, a specifying unit 48, a second generation unit 50, and a display controller 52. The CPU 20 executes the support program 30 to function as the acquisition unit 40, the deformation unit 42, the first generation unit 44, the derivation unit 46, the specifying unit 48, the second generation unit 50, and the display controller 52.

The acquisition unit 40 acquires the three-dimensional medical image 32 from the storage unit 22. In addition, the acquisition unit 40 sequentially acquires the fluoroscopic images captured by the fluoroscopic image capturing device 3 at a predetermined frame rate via the network I/F 25.

The deformation unit 42 deforms the three-dimensional medical image 32 by performing the registration of the three-dimensional medical image 32 and the fluoroscopic image that are acquired by the acquisition unit 40. For example, the deformation unit 42 derives a deformation parameter of an affine transformation such that the positions of the sites shown in the three-dimensional medical image 32 and the fluoroscopic image, such as the bronchus and the pulmonary artery, are subjected to the registration. Then, the deformation unit 42 deforms the three-dimensional medical image 32 using the derived deformation parameter. Note that the deformation unit 42 may perform the registration of the three-dimensional medical image 32 and the fluoroscopic image by using a known method other than the affine transformation such as a rigid body transformation or a non-linear non-rigid body transformation. In addition, the deformation unit 42 may perform the registration of the three-dimensional medical image 32 and the fluoroscopic image by using a trained model obtained by machine learning such as deep learning.

The first generation unit 44 acquires a three-dimensional pathway that is three-dimensional information of a bronchial lumen as an example of a pathway through which the endoscope 6A passes, on the basis of the three-dimensional medical image 32 after the deformation by the deformation unit 42. Specifically, the first generation unit 44 generates the three-dimensional pathway data 34, which is a set of voxel data, by performing three-dimension (3D) modeling that numerically describes a three-dimensional shape of a body of the subject H on the basis of the deformed three-dimensional medical image 32. The voxel data is a unit of a pixel in a three-dimensional space, and has three-dimensional coordinate information and a pixel value. In the present embodiment, a bronchus is included in the imaging range of the three-dimensional medical image 32. That is, the three-dimensional pathway data 34 includes a three-dimensional pathway that is three-dimensional information of the bronchial lumen. The three-dimensional pathway is a set of voxel data corresponding to the bronchial lumen.

In addition, in the present embodiment, a lesion region as a treatment target, such as a lung nodule, is designated in advance as a region of interest. The three-dimensional medical image 32 also includes a lesion region. Therefore, the three-dimensional pathway data 34 also includes a three-dimensional position of the lesion region. Note that the lesion is not limited to the lung nodule and may be a tumor or the like. In addition, the region of interest is not limited to the lesion region and may be an anatomical region. The anatomical region means, for example, a specific region including an anatomical structure of a living body. The anatomical region includes, for example, a bone, a muscle, an organ, a blood vessel, and the like.

The derivation unit 46 acquires the three-dimensional pathway from the three-dimensional pathway data 34. In addition, the derivation unit 46 derives a feature amount (hereinafter, referred to as a "first feature amount") representing a relationship between a reference point in the three-dimensional space and the three-dimensional pathway. Hereinafter, a specific example of the derivation processing of the first feature amount by the derivation unit 46 will be described.

The derivation unit 46 acquires a visual line direction for projecting the three-dimensional pathway onto the two-dimensional plane. The visual line direction is used in a case where the second generation unit 50 to be described later generates a composite image. In addition, the derivation unit 46 sets the reference point on the three-dimensional pathway. For example, the derivation unit 46 sets a position of the treatment tool of the endoscope 6A on the three-dimensional pathway as the reference point. For example, the operator designates the position of the treatment tool on the fluoroscopic image displayed on the display 23 via the input device 24. The derivation unit 46 sets the designated position of the treatment tool on the fluoroscopic image as the reference point on the three-dimensional pathway by performing the back projection.

In addition, the derivation unit 46 derives, as the first feature amount, a feature amount representing a relative positional relationship between the reference point and the three-dimensional pathway in the visual line direction. As described above, the three-dimensional pathway is a set of voxel data, and the voxel data has three-dimensional coordinate information. The derivation unit 46 derives, as the first feature amount, the distance between the reference point and the three-dimensional pathway along the visual line direction on the basis of the visual line direction, the three-dimensional coordinates of the reference point, and the three-dimensional coordinate information of each voxel data constituting the three-dimensional pathway. In the present embodiment, the derivation unit 46 assigns a negative sign to a distance to the three-dimensional pathway on a side closer to a viewpoint position than the reference point, that is, on the nearer side of the reference point as viewed from the viewpoint position. In addition, the derivation unit 46 assigns a positive sign to a distance to the three-dimensional pathway on a side farther from the viewpoint position than the reference point, that is, on the farther side of the reference point as viewed from the viewpoint position. Note that the derivation unit 46 may treat the distance as an absolute value, and may assign information indicating that the distance to the three-dimensional pathway is on a side closer to the viewpoint position than the reference point or on a side farther from the viewpoint position than the reference point, to the absolute value representing the distance.

In addition, the derivation unit 46 acquires the three-dimensional position of the lesion region from the three-dimensional pathway data 34. In addition, the derivation unit 46 derives a feature amount (hereinafter, referred to as a "second feature amount") representing a relationship between the reference point and the three-dimensional position of the lesion region. Similarly to the first feature amount, the derivation unit 46 derives, as the second feature amount, a feature amount representing a relative positional relationship between the reference point and the three-dimensional position of the lesion region in the visual line direction. That is, the derivation unit 46 derives, as the second feature amount, the distance between the reference point and the three-dimensional position of the lesion region along the visual line direction on the basis of the visual line direction, the three-dimensional coordinates of the reference point, and the three-dimensional position of the lesion region.

The specifying unit 48 acquires the focused pathway on the three-dimensional pathway from the three-dimensional pathway data 34. Specifically, the specifying unit 48 derives a distance between the three-dimensional pathway and the lesion region. This distance may be a distance in the three-dimensional space represented by the three-dimensional pathway data 34 or a distance along the visual line direction. Then, the specifying unit 48 specifies, as the focused pathway, a pathway connecting a point at which the derived distance on the three-dimensional pathway is equal to or less than a threshold value to the reference point, and acquires the focused pathway from the three-dimensional pathway data 34. That is, the focused pathway corresponds to a pathway toward the lesion region in the three-dimensional pathway. The threshold value in this case is set in advance according to, for example, the type of lesion, the type of organ including the pathway through which the medical instrument passes, and the like.

The second generation unit 50 generates a composite image in which the three-dimensional pathway is superimposed on the fluoroscopic image. Hereinafter, a specific example of the generation processing of the composite image by the second generation unit 50 will be described.

First, the second generation unit 50 sets a viewpoint position in a case of projecting the three-dimensional pathway onto the two-dimensional plane. The two-dimensional plane is a virtually set two-dimensional projection plane. Since the three-dimensional pathway is superimposed on the fluoroscopic image acquired by the X-ray detector 3C, the two-dimensional plane corresponds to an X-ray detection surface of the X-ray detector 3C. For example, the second generation unit 50 sets a position corresponding to a position of the X-ray source 3B with respect to the two-dimensional plane as the viewpoint position on the basis of the relative positional relationship between the X-ray detector 3C and the X-ray source 3B. A direction from the viewpoint position to the point on the two-dimensional plane is the visual line direction for projecting the three-dimensional pathway onto the two-dimensional plane.

The second generation unit 50 projects the three-dimensional pathway onto the two-dimensional plane by a known method such as a perspective projection method, performs registration using known regions such as a bronchus, a pulmonary artery, and a lesion region, and generates a composite image in which the three-dimensional pathway is superimposed on the fluoroscopic image. In this case, the second generation unit 50 superimposes the lesion region included in the three-dimensional pathway data 34 on the fluoroscopic image, similarly to the three-dimensional pathway.

The second generation unit 50 assigns color information representing a color different from the binary color used in the fluoroscopic image to the focused pathway on the three-dimensional pathway in the composite image. Specifically, the second generation unit 50 assigns color information representing a color corresponding to the first feature amount derived by the derivation unit 46 to the focused pathway. In addition, the second generation unit 50 assigns color information representing a color corresponding to the second feature amount derived by the derivation unit 46 to the lesion region, similarly to the focused pathway, in the composite image.

Figure 4:
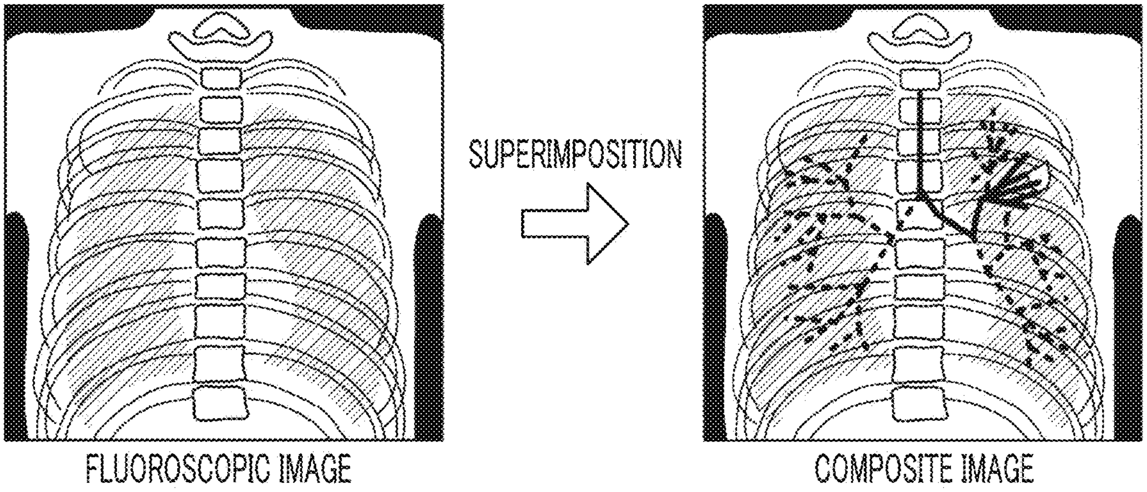
FIG. 4 is a diagram illustrating an example of a fluoroscopic image and a composite image.

The display controller 52 performs control of displaying the composite image generated by the second generation unit 50 on the display 23. FIG. 4 shows an example of the fluoroscopic image and the composite image. As illustrated in FIG. 4, in the composite image, a color corresponding to the first feature amount is assigned to the focused pathway superimposed on the fluoroscopic image, and a color corresponding to the second feature amount is assigned to the lesion region. A thick solid line portion in the composite image in FIG. 4 represents the focused pathway. A thick broken line portion in the composite image of FIG. 4 represents a pathway other than the focused pathway on the three-dimensional pathway. That is, in the control of displaying the composite image, the display controller 52 performs control of displaying the focused pathway in an emphasized manner as compared with a pathway other than the focused pathway on the three-dimensional pathway.

Figure 5:
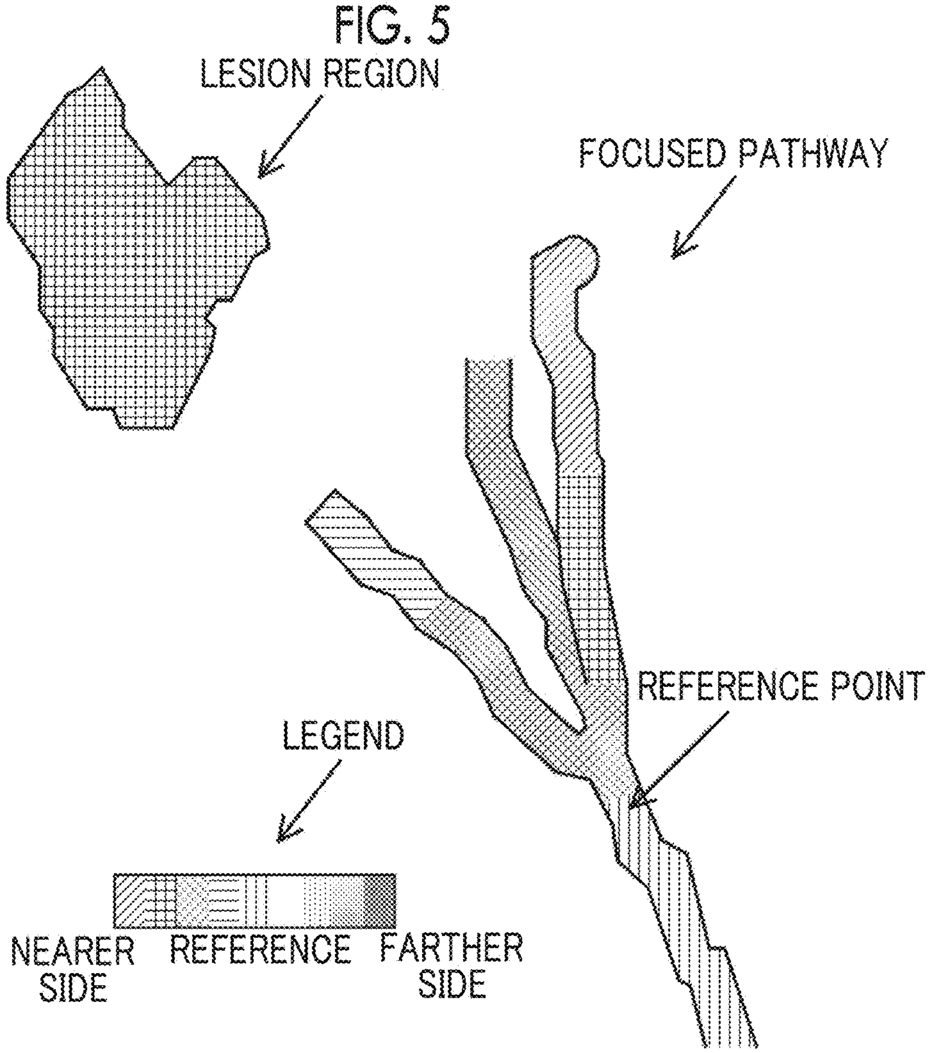
FIG. 5 is a diagram illustrating an example of a portion of a lesion region and a focused pathway in a composite image.

FIG. 5 illustrates an example of a diagram in which a portion of the lesion region and the focused pathway in the composite image is enlarged. As illustrated in FIG. 5, in the composite image, a color corresponding to the first feature amount is assigned to each pixel representing the focused pathway, the first feature amount representing a relative positional relationship between a point of the focused pathway corresponding to each pixel and the reference point in the visual line direction. That is, the display controller 52 varies the display aspect of the three-dimensional pathway in the composite image according to the first feature amount. Therefore, the operator can ascertain the information on the depth direction of the pathway through which the endoscope 6A passes by observing the color of the focused pathway on the three-dimensional pathway. In addition, since the reference point is set to the position of the treatment tool attached to the distal end of the endoscope 6A, the operator can ascertain the information on the depth direction with the treatment tool as a reference.

In addition, as illustrated in FIG. 5, in the composite image, a color corresponding to the second feature amount is assigned to each pixel representing the lesion region, the second feature amount representing a relative positional relationship between a point of the lesion region corresponding to each pixel and the reference point in the visual line direction. That is, the display controller 52 varies the display aspect of the lesion region in the composite image according to the second feature amount. Therefore, the operator can ascertain the information on the depth direction of the lesion region as the treatment target by observing the color of the lesion region.

Figure 6:
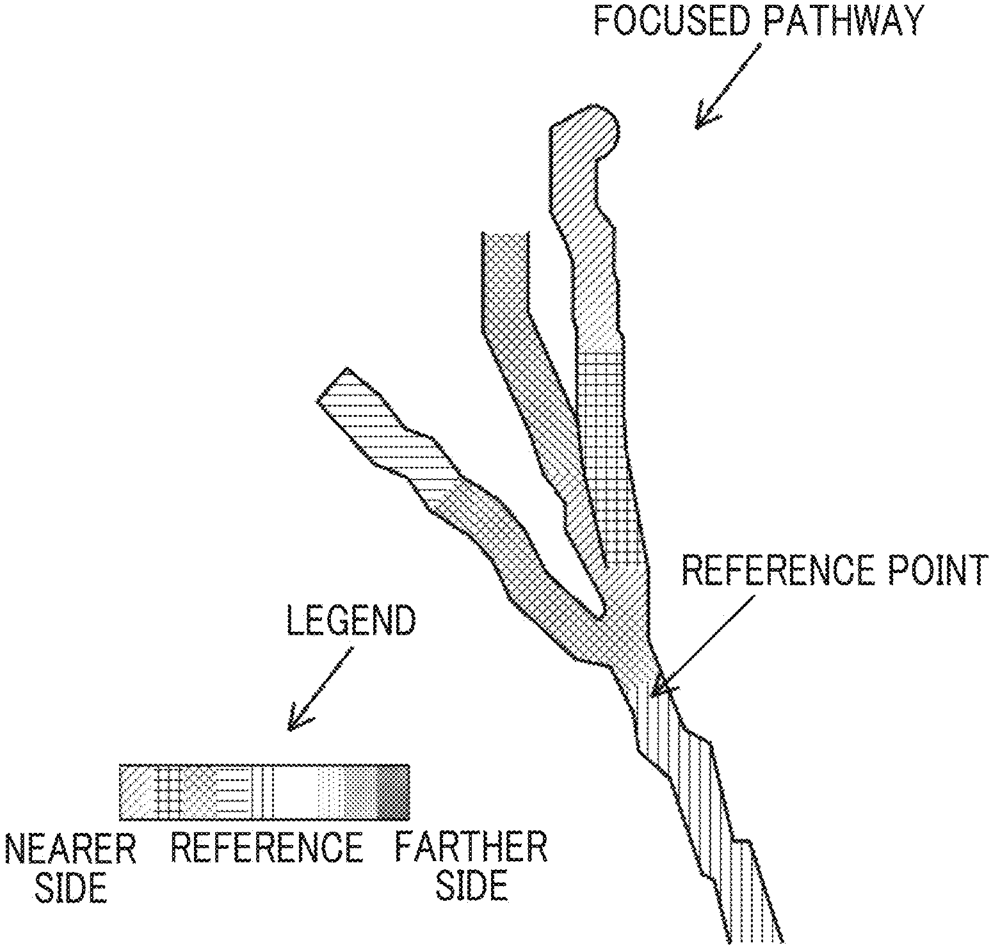
FIG. 6 is a diagram illustrating an example of a portion of a focused pathway in a composite image.

Note that as illustrated in FIG. 5, the display controller 52 may perform control of displaying a legend of colors corresponding to the first feature amount and the second feature amount on the same screen as the composite image. In addition, as illustrated in FIG. 6, the color information corresponding to the second feature amount may not be assigned to the lesion region.

Next, an action of the support device 1 will be described with reference to FIG. 7. The CPU 20 executes the support program 30 to execute the insertion support processing illustrated in FIG. 7. The insertion support processing is executed, for example, in a case where the position of the treatment tool on the fluoroscopic image is designated by the operator.

Figure 7:
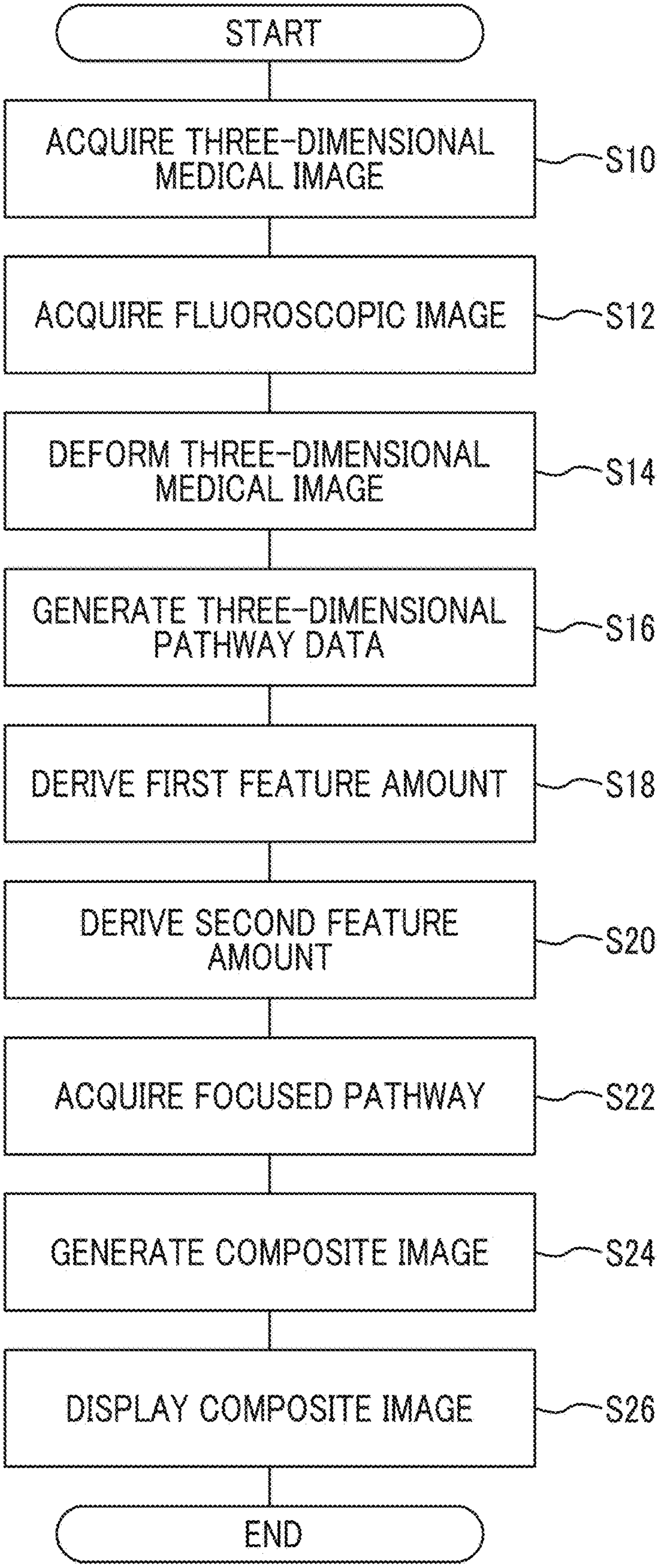
FIG. 7 is a flowchart illustrating an example of insertion support processing.

In step S10 of FIG. 7, the acquisition unit 40 acquires the three-dimensional medical image 32 from the storage unit 22. In step S12, the fluoroscopic image captured by the fluoroscopic image capturing device 3 at a predetermined frame rate is acquired via the network I/F 25. In step S14, the deformation unit 42 deforms the three-dimensional medical image 32 by performing the registration of the three-dimensional medical image 32 acquired in step S10 and the fluoroscopic image acquired in step S12, as described above.

In step S16, as described above, the first generation unit 44 generates the three-dimensional pathway data 34 on the basis of the three-dimensional medical image 32 after the deformation by the processing of step S14. In step S18, the derivation unit 46 acquires the three-dimensional pathway from the three-dimensional pathway data 34 generated in step S16. In addition, the derivation unit 46 derives the first feature amount representing the relationship between the three-dimensional pathway and the reference point in the three-dimensional space as described above.

In step S20, the derivation unit 46 acquires the three-dimensional position of the lesion region from the three-dimensional pathway data 34 generated in step S16. In addition, the derivation unit 46 derives the second feature amount representing the relationship between the reference point and the three-dimensional position of the lesion region as described above. In step S22, the specifying unit 48 acquires the focused pathway on the three-dimensional pathway from the three-dimensional pathway data 34 generated in step S16, as described above.

In step S24, the second generation unit 50 generates the composite image in which the three-dimensional pathway and the lesion region are superimposed on the fluoroscopic image, as described above. The second generation unit 50 assigns color information representing a color corresponding to the first feature amount derived in step S18, to the focused pathway acquired in step S22, in the composite image. In addition, the second generation unit 50 assigns color information representing a color corresponding to the second feature amount derived in step S20, to the lesion region in the composite image. In step S26, the display controller 52 performs control of displaying the composite image generated in step S24 on the display 23. In a case where the processing of step S26 ends, the insertion support processing ends.

As described above, according to the present embodiment, it is possible to effectively support the procedure of inserting the medical instrument into the tubular structure.

Figure 8:
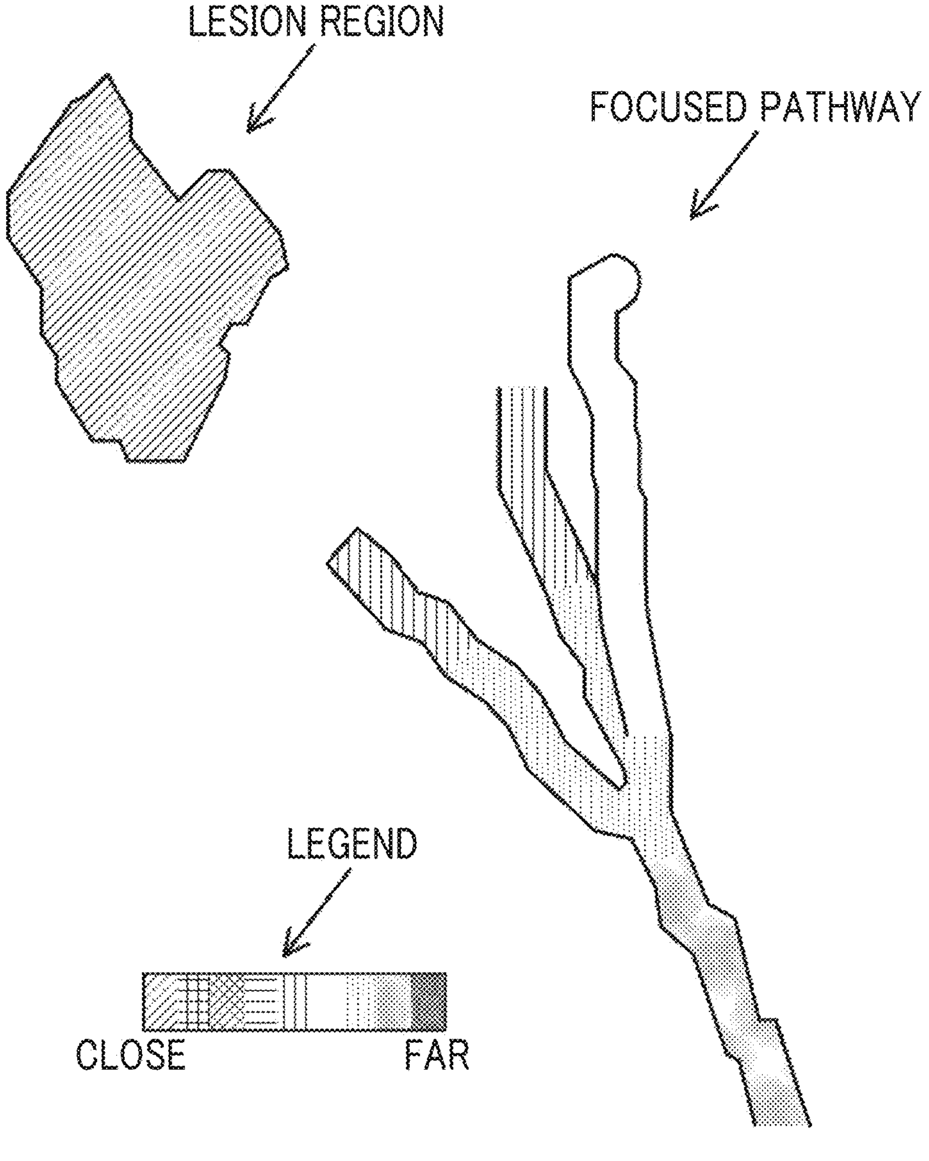
FIG. 8 is a diagram illustrating an example of a portion of a lesion region and a focused pathway in a composite image according to a modification example.

Note that in the above-described embodiment, a case has been described in which the derivation unit 46 sets the position of the treatment tool of the endoscope 6A on the three-dimensional pathway as the reference point, but the disclosed technology is not limited to this aspect. For example, the derivation unit 46 may set the position of a camera of the endoscope 6A on the three-dimensional pathway as the reference point. In addition, for example, the derivation unit 46 may set a three-dimensional position of the region of interest that is not located on the three-dimensional pathway as the reference point. FIG. 8 shows an example of a composite image in a case where a predetermined point in the lesion region, which is an example of a region of interest, is set as the reference point. As illustrated in FIG. 8, in this form example, the operator can ascertain whether each position on the focused pathway is a position close to or far from the lesion region.

In addition, in the above-described embodiment, a case has been described in which a feature amount representing a relative positional relationship between the reference point and the three-dimensional pathway in the visual line direction is applied as the first feature amount, but the disclosed technology is not limited to this aspect. For example, as the first feature amount, a distance between the reference point and the three-dimensional pathway in the three-dimensional space may be applied. In this form example, the derivation unit 46 derives a distance between the reference point and the three-dimensional pathway in the three-dimensional space on the basis of the three-dimensional coordinates of the reference point and the three-dimensional coordinates of the three-dimensional pathway.

In addition, in the above-described embodiment, a case has been described in which a pathway connecting the reference point to a point at which the distance to the region of interest on the three-dimensional pathway is equal to or less than the threshold value is applied as the focused pathway, but the disclosed technology is not limited to this aspect. For example, as the focused pathway, a pathway registered in advance as preoperative information may be applied.

In addition, in the above-described embodiment, a case has been described in which the fluoroscopic image captured by the fluoroscopic image capturing device 3, that is, the radiation image acquired by actually performing irradiation with the radiation is applied as the two-dimensional medical image, but the disclosed technology is not limited to this aspect. For example, as the two-dimensional medical image, a virtual radiation image generated from a three-dimensional medical image may be applied.

In addition, in the above-described embodiment, a case has been described in which the display controller 52 varies the display aspect by making the colors of the three-dimensional pathway and the region of interest different, but the disclosed technology is not limited to this aspect. For example, the display controller 52 may vary the display aspect by varying the transparency of the three-dimensional pathway and the region of interest, the thickness of the frame line, the type of the frame line, and the like. In a case of varying the transparency, a form in which the transparency is increased as the distance from the reference point is increased is exemplified.

In addition, in the above-described embodiment, a case has been described in which the display controller 52 performs control of displaying the focused pathway in an emphasized manner by performing control of coloring and displaying the focused pathway of the composite image, but the disclosed technology is not limited to this aspect. For example, the display controller 52 may perform control of displaying the focused pathway in an emphasized manner by varying the transparency of the focused pathway, the thickness of the frame line, the type of the frame line, and the like.

In addition, in the above-described embodiment, a case has been described in which the bronchus is applied as the tubular structure and the bronchial lumen is applied as the path way through which the medical instrument passes, but the disclosed technology is not limited to this aspect. For example, a blood vessel may be applied as the tubular structure, and a blood vessel lumen may be applied as the pathway through which the medical instrument passes.

In addition, in the above-described embodiment, for example, as a hardware structure of a processing unit that executes various kinds of processing, such as each functional unit of the support device 1, following various processors may be used. The various processors include, for example, a programmable logic device (PLD) that is a processor of which the circuit configuration can be changed after manufacture, such as a field-programmable gate array (FPGA), and a dedicated electric circuit that is a processor having a dedicated circuit configuration designed to execute specific processing, such as an application specific integrated circuit (ASIC), in addition to the CPU that is a general-purpose processor which executes software (programs) to function as various processing units as described above.

One processing unit may be composed of one of the various processors or may be composed of a combination of two or more processors of the same type or different types (for example, a combination of a plurality of FPGAs or a combination of a CPU and an FPGA). In addition, a plurality of processing units may be configured by one processor.

As an example in which a plurality of processing units are configured by one processor, first, there is a form in which one processor is configured by a combination of one or more CPUs and software as typified by a computer, such as a client or a server, and this processor functions as a plurality of processing units. Second, as represented by a system on chip (SoC), a form of using a processor that implements functions of the entire system including the plurality of processing units in one integrated circuit (IC) chip is possible. In this manner, various processing units are composed of one or more of the above-described various processors as hardware structures.

Furthermore, as the hardware structure of the various processors, more specifically, an electrical circuit (circuitry) in which circuit elements such as semiconductor elements are combined can be used.

In addition, in the above-described embodiment, the support program 30 has been described as being stored (installed) in the storage unit 22 in advance, but the present disclosure is not limited thereto. The support program 30 may be provided in a form of being recorded on a recording medium such as a compact disc read only memory (CD-ROM), a digital versatile disc read only memory (DVD-ROM), and a universal serial bus (USB) memory. In addition, the support program 30 may be downloaded from an external device via a network.

What is claimed is:

1. A support device that includes at least one processor and is configured to support insertion of a medical instrument into a tubular structure, wherein the at least one processor is configured to:

acquire a two-dimensional medical image, and a three-dimensional pathway that is three-dimensional information on a pathway through which the medical instrument is configured to pass, derive a first feature amount representing a relationship between a reference point in a three-dimensional space and the three-dimensional pathway, perform control of displaying a composite image in which the three-dimensional pathway is superimposed on the two-dimensional medical image, vary a display aspect of the three-dimensional pathway in the composite image according to the first feature amount; and acquire a visual line direction for projecting the three-dimensional pathway onto a two-dimensional plane, wherein the first feature amount is a feature amount representing a relative positional relationship between the reference point and the three-dimensional pathway in the visual line direction.

2. The support device according to claim 1, wherein the at least one processor is configured to:

acquire a three-dimensional position of a region of interest, derive a second feature amount representing a relationship between the reference point and the three-dimensional position of the region of interest, perform control of displaying the composite image in which the region of interest is superimposed on the two-dimensional medical image, and vary a display aspect of the region of interest in the composite image according to the second feature amount.

3. The support device according to claim 2, wherein the at least one processor is configured to acquire a visual line direction for projecting the three-dimensional pathway onto a two-dimensional plane, and the second feature amount is a feature amount representing a relative positional relationship between the reference point and the three-dimensional position of the region of interest in the visual line direction.

4. The support device according to claim 2, wherein the reference point is the three-dimensional position of the region of interest.

5. The support device according to claim 1, wherein the reference point is a point on the three-dimensional pathway.

6. The support device according to claim 5, wherein the reference point is a position of the medical instrument on the three-dimensional pathway.

7. The support device according to claim 6, wherein the medical instrument is an endoscope including a treatment tool, and the reference point is a position of the treatment tool on the three-dimensional pathway.

8. The support device according to claim 6, wherein the medical instrument is an endoscope including a camera, and the reference point is a position of the camera on the three-dimensional pathway.

9. The support device according to claim 1, wherein the first feature amount is a distance between the reference point and the three-dimensional pathway in the three-dimensional space.

10. The support device according to claim 1, wherein the at least one processor is configured to:

acquire a focused pathway on the three-dimensional pathway, and in the control of displaying the composite image, perform control of displaying the focused pathway in an emphasized manner as compared with a pathway other than the focused pathway on the three-dimensional pathway.

11. The support device according to claim 10, wherein the focused pathway is a pathway connecting the reference point to a point at which a distance to the region of interest on the three-dimensional pathway is equal to or less than a threshold value.

12. The support device according to claim 10, wherein the focused pathway is a pathway registered in advance as preoperative information.

13. The support device according to claim 1, wherein a pathway through which the medical instrument is configured to pass is a bronchial lumen.

14. The support device according to claim 1, wherein the two-dimensional medical image is an image obtained by radiographic fluoroscopy.

15. The support device according to claim 1, wherein the three-dimensional pathway is a bronchial lumen in a three-dimensional medical image, and the two-dimensional medical image is a virtual radiation image generated from the three-dimensional medical image.

16. The support device according to claim 1, wherein the at least one processor is configured to:

acquire a three-dimensional medical image including a pathway through which the medical instrument passes, deform the three-dimensional medical image by performing registration of the three-dimensional medical image and the two-dimensional medical image, and acquire the three-dimensional pathway on the basis of the deformed three-dimensional medical image.

17. A support method of processing executed by a processor of a support device that includes at least one processor and is configured to support insertion of a medical instrument into a tubular structure, the method comprising:

acquiring a two-dimensional medical image, and a three-dimensional pathway that is three-dimensional information on a pathway through which the medical instrument passes;

deriving a first feature amount representing a relationship between a reference point in a three-dimensional space and the three-dimensional pathway;

performing control of displaying a composite image in which the three-dimensional pathway is superimposed on the two-dimensional medical image;

varying a display aspect of the three-dimensional pathway in the composite image according to the first feature amount; and acquiring a visual line direction for projecting the three-dimensional pathway onto a two-dimensional plane, wherein the first feature amount is a feature amount representing a relative positional relationship between the reference point and the three-dimensional pathway in the visual line direction.

18. A non-transitory computer-readable storage medium storing a support program for causing a processor of a support device that includes at least one processor and supports insertion of a medical instrument into a tubular structure, to execute processing comprising:

acquiring a two-dimensional medical image, and a three-dimensional pathway that is three-dimensional information on a pathway through which the medical instrument passes;

deriving a first feature amount representing a relationship between a reference point in a three-dimensional space and the three-dimensional pathway;

performing control of displaying a composite image in which the three-dimensional pathway is superimposed on the two-dimensional medical image;

varying a display aspect of the three-dimensional pathway in the composite image according to the first feature amount; and acquiring a visual line direction for projecting the three-dimensional pathway onto a two-dimensional plane, wherein the first feature amount is a feature amount representing a relative positional relationship between the reference point and the three-dimensional pathway in the visual line direction.

* * * * *